United States Patent
Ringenbach et al.

(10) Patent No.: US 10,722,452 B2
(45) Date of Patent: Jul. 28, 2020

(54) **COSMETIC USE OF AN INGREDIENT DERIVED FROM *MARRUBIUM VULGARE***

(71) Applicant: Sederma, Le Perray en Yvelines (FR)

(72) Inventors: Caroline Ringenbach, Rambouillet (FR); Emmanuel Doridot, Montigny le Bretonneux (FR); Philippe Mondon, Montrouge (FR)

(73) Assignee: Sederma, Le Perray en Yvelines (FR)

( * ) Notice: Subject to any disclaimer, the term of this patent is extended or adjusted under 35 U.S.C. 154(b) by 0 days.

(21) Appl. No.: 16/086,368

(22) PCT Filed: Mar. 21, 2017

(86) PCT No.: PCT/IB2017/051617
§ 371 (c)(1),
(2) Date: Sep. 19, 2018

(87) PCT Pub. No.: WO2017/163174
PCT Pub. Date: Sep. 28, 2017

(65) Prior Publication Data
US 2019/0099362 A1    Apr. 4, 2019

(30) Foreign Application Priority Data
Mar. 23, 2016  (FR) ..................... 16 70126

(51) Int. Cl.
| | | |
|---|---|---|
| *A61K 36/00* | (2006.01) | |
| *A61K 8/9789* | (2017.01) | |
| *A61Q 19/08* | (2006.01) | |
| *A61K 8/97* | (2017.01) | |
| *A61Q 19/00* | (2006.01) | |

(52) U.S. Cl.
CPC .............. *A61K 8/9789* (2017.08); *A61K 8/97* (2013.01); *A61Q 19/00* (2013.01); *A61Q 19/008* (2013.01); *A61Q 19/08* (2013.01)

(58) Field of Classification Search
None
See application file for complete search history.

(56) References Cited

U.S. PATENT DOCUMENTS

2009/0208544 A1* 8/2009 Ennamany ............... A61K 8/11
424/401

FOREIGN PATENT DOCUMENTS

| EP | 2319914 A1 | 5/2011 | |
| FR | 2679141 A1 * | 1/1993 | ............... A61K 8/44 |
| KR | 2015056314 A * | 5/2015 | |
| WO | 9745099 A1 | 12/1997 | |
| WO | WO 2003105876 A1 * | 12/2003 | |
| WO | 2014080376 A2 | 5/2014 | |
| WO | 2015181688 A1 | 12/2015 | |

OTHER PUBLICATIONS

Sahpaz, Isolation and pharmacological activity of phenylpropanoid esters from Marrubium vulgare. Journal of ethnopharmacology, (Mar. 2002) vol. 79, No. 3, pp. 389-392 (Year: 2002).*
International Cosmetic Ingredient Dictionary and Handbook, 16th Edition, 2016, vol. 1—61 pages.
International Search Report and Written Opinion for International Application No. PCT/IB2017/051617, dated Jun. 27, 2017—11 pages.

\* cited by examiner

*Primary Examiner* — Qiuwen Mi
(74) *Attorney, Agent, or Firm* — RatnerPrestia

(57) ABSTRACT

The invention proposes to use a plant material derived from *Marrubium vulgare* for a non-therapeutic cosmetic treatment for tightening skin pores, said plant material comprising an effective amount of Forsythoside B as the active molecule. The plant material is preferably constituted of a cellular extract of dedifferentiated plant cells freed from cellular debris. This treatment is particularly intended for refining skin grain and/or for treating skin with an oily tendency.

7 Claims, 1 Drawing Sheet

Specification includes a Sequence Listing.

```
                    SEQUENCE LISTING

<160> NUMBER OF SEQ ID NOS: 25

<210> SEQ ID NO 1
<211> LENGTH: 4
<212> TYPE: PRT
<213> ORGANISM: artificial sequence
<220> FEATURE:
<223> OTHER INFORMATION: synthetic peptide

<400> SEQUENCE: 1

Arg Ser Arg Lys
1

<210> SEQ ID NO 2
<211> LENGTH: 4
<212> TYPE: PRT
<213> ORGANISM: artificial sequence
<220> FEATURE:
<223> OTHER INFORMATION: synthetic peptide

<400> SEQUENCE: 2

Gly Gln Pro Arg
1

<210> SEQ ID NO 3
<211> LENGTH: 4
<212> TYPE: PRT
<213> ORGANISM: artificial sequence
<220> FEATURE:
<223> OTHER INFORMATION: synthetic peptide

<400> SEQUENCE: 3

Lys Thr Phe Lys
1

<210> SEQ ID NO 4
<211> LENGTH: 4
<212> TYPE: PRT
<213> ORGANISM: Artificial sequence
<220> FEATURE:
```

```
<223> OTHER INFORMATION: Synthetic peptide

<400> SEQUENCE: 4

Lys Thr Ala Lys
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

Lys Ala Tyr Lys
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide

<400> SEQUENCE: 6

Lys Phe Tyr Lys
1

<210> SEQ ID NO 7
<211> LENGTH: 5
<212> TYPE: PRT
<213> ORGANISM: artificial sequence
<220> FEATURE:
<223> OTHER INFORMATION: synthetic peptide

<400> SEQUENCE: 7

Lys Thr Thr Lys Ser
1               5

<210> SEQ ID NO 8
<211> LENGTH: 6
<212> TYPE: PRT
<213> ORGANISM: artificial sequence
<220> FEATURE:
<223> OTHER INFORMATION: Synthetic peptide

<400> SEQUENCE: 8

Gly Lys Thr Thr Lys Ser
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Val Gly Val Ala Pro Gly
1               5

<210> SEQ ID NO 10
<211> LENGTH: 4
<212> TYPE: PRT
<213> ORGANISM: artificial sequence
<220> FEATURE:
<223> OTHER INFORMATION: synthetic peptide
```

```
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 10

Gly Gln Pro Arg
1

<210> SEQ ID NO 11
<211> LENGTH: 4
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 11

Lys Thr Phe Lys
1

<210> SEQ ID NO 12
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 12

Lys Thr Phe Lys
1

<210> SEQ ID NO 13
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 13

Lys Thr Ala Lys
1

<210> SEQ ID NO 14
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 14
```

```
Lys Ala Tyr Lys
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 15

Lys Phe Tyr Lys
1

<210> SEQ ID NO 16
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 16

Lys Thr Thr Lys Ser
1               5

<210> SEQ ID NO 17
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (5)..(5)
<223> OTHER INFORMATION: Xaa being either a Proline P or a Leucine L.

<400> SEQUENCE: 17

Tyr Gly Gly Phe Xaa
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (6)..(6)
<223> OTHER INFORMATION: Xaa being Trp, Phe, Tyr, Tic, 7-hydroxy-Tic or
      Tpi
```

<400> SEQUENCE: 18

His Leu Asp Ile Ile Xaa
1               5

<210> SEQ ID NO 19
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 19

Val Gly Val Ala Pro Gly
1               5

<210> SEQ ID NO 20
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 20

Gly Lys Thr Thr Lys Ser
1               5

<210> SEQ ID NO 21
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation on the N-terminal end

<400> SEQUENCE: 21

Glu Glu Met Gln Arg Arg
1               5

<210> SEQ ID NO 22
<211> LENGTH: 5
<212> TYPE: PRT
<213> ORGANISM: artificial sequence
<220> FEATURE:
<223> OTHER INFORMATION: synthetic peptide

<400> SEQUENCE: 22

Tyr Ala Gly Phe Leu
1               5

<210> SEQ ID NO 23
<211> LENGTH: 4
<212> TYPE: PRT
<213> ORGANISM: artificial sequence
<220> FEATURE:
<223> OTHER INFORMATION: synthetic peptide

```
<400> SEQUENCE: 23

Ala His Ser His
1

<210> SEQ ID NO 24
<211> LENGTH: 6
<212> TYPE: PRT
<213> ORGANISM: artificial sequence
<220> FEATURE:
<223> OTHER INFORMATION: synthetic peptide

<400> SEQUENCE: 24

Ser Ile Lys Val Ala Val
1               5

<210> SEQ ID NO 25
<211> LENGTH: 6
<212> TYPE: PRT
<213> ORGANISM: artificial sequence
<220> FEATURE:
<223> OTHER INFORMATION: synthetic peptide

<400> SEQUENCE: 25

Gly Pro Gln Gly Pro Gln
1               5
```

US 10,722,452 B2

COSMETIC USE OF AN INGREDIENT DERIVED FROM *MARRUBIUM VULGARE*

This application is the U.S. National Phase application of PCT International Application No. PCT/IB2017/051617, filed Mar. 21, 2017, which claims the benefit of priority of French Patent Application No. FR 1670126, filed Mar. 23, 2016, the contents of which are incorporated herein by reference in their entirety for all purposes.

TECHNICAL FIELD

The present invention relates to the use of a plant material derived from a plant for a cosmetic treatment intended to improve the appearance and general condition of the skin or the scalp.

The present invention can be applied, for example, to the cosmetic and hygiene and personal care industries which are always in demand for new products, in particular in increasing demand for new active ingredients derived from plants. With such active ingredients it is possible to combine efficacy, limited irritation and allergy risks, reduced side effects, biodegradability, with the possibilities of labeling/certifications and adequacy with logic of sustainable development and/or fair trade.

BACKGROUND ART

The aim of the present invention is more specifically to propose a plant material derived from a plant that is effective in beautifying the skin by treating its pores.

The skin has many pores on its surface whose function is to remove excess of sebum and impurities from the skin such as dead cells and sweat. When the skin is too greasy or the rate of keratinocyte proliferation is too high, the pores can become clogged and then enlarged or dilated. The pores become then more visible and make the grain of the skin irregular and unsightly.

As part of a purely cosmetic treatment, it is also important to be able to act upstream in order to prevent the last stage even more unsightly where comedones formed in the pores are transformed into acne pimples, which may then require medical treatment.

*Marrubium vulgare*, also known as White Horehound or Marrubio, is an edible herbaceous plant of the Lamiaceae family which grows spontaneously in the temperate regions of Europe, America and Asia. The medicinal properties of the White Horehound were known to the Romans and Arabs, and the plant has often been used by popular medicine as a remedy for respiratory and digestive disorders. Besides, in topical application, the plant is known to possess anti-inflammatory properties.

A cosmetic ingredient comprising *Marrubium vulgare* cells obtained by in vitro culture and suspended in glycerin and xanthan gum has already been proposed as an anti-pollution/detoxifying active agent thanks to properties against free radicals and a stimulation of the self-defense of the skin. The technique for in vitro manufacturing plant cells makes it possible to advantageously obtain a reproducible composition rich in phenylpropanoids, such as Forsythoside B (also described in the patent application EP2319914), and in phystosterols, amino acids and polysaccharides.

SUMMARY OF THE INVENTION

The present invention provides the use of a cosmetic ingredient comprising a plant material derived from *Marrubium vulgare* for a non-therapeutic cosmetic treatment to tighten skin pores. Thanks to this treatment, the skin is visibly more beautiful. Its grain is refined, more homogeneous thanks to a smoothing effect of the micro-relief. Its greasy/shiny appearance, which was due to the sebum present in the pores, is decreased.

Results of in vivo tests demonstrating these effects are presented in more details hereinafter in the specification.

According to the invention, a plant material derived from *Marrubium vulgare* can be obtained by conventional extraction methods directly from the whole plant or parts thereof, or by in vitro culture methods, either by cell culture or by tissue culture, from cellular or tissue lines derived from different organs of the plant.

According to the invention, the plant material is preferably obtained by in vitro plant culture. Indeed, obtaining by in vitro culture has many advantages over the agro-industrial route (field crop cultivation and subsequent extraction in factory). Due to the complete control of crop conditions, the materials obtained by in vitro culture are free from toxic substances (herbicides, pesticides, fertilizers, heavy metals and other contaminants, such as those which may be derived from plant pests). Moreover, strict control of in vitro culture conditions reduces the risk of spontaneous variation of the strain and guarantees a reproducible profile of secondary metabolites which correspond to the molecules of interest desired, in contrast to the field crop where the problem arises of the variability, linked to climatic, meteorological and geographical conditions and their hazards. Moreover, this in vitro technology is free from obstacles such as the natural life cycle of the plant and the seasonal production of secondary metabolites, allowing a better security and fast supply. Still moreover, the environmental impact is minimal because it substantially limits water consumption, avoiding consumption of arable land, and preventing soil pollution. In addition, biodiversity is preserved since a plant or even a seed is enough to initiate a new in vitro culture. Finally, this technology offers the possibility of directing cellular metabolism towards the production of molecules of interest (in particular by elicitation of cultures) and to carry out controlled and relatively rapid protocols in order to increase the yields of certain molecules, particularly those produced in small amounts in the plant.

Existing techniques in the domain of in vitro culture of plants include in particular:

The culture of undifferentiated or dedifferentiated cells (hereinafter referred to as plant cell culture): this type of method firstly involves the creation of highly proliferating cell lines in agar medium, either from meristematic cells which are undifferentiated cells or from dedifferentiated cells (growing in the form of callus, following the removal of a plant fragment, leaf, stem, root or other). These lines are then cultured in liquid medium so as to substantially increase the biomass. At the end of the growth cycle and under conditions of the medium to be defined and optimized (research, for example, of the good elicitation medium), the cell biomass will synthesize the molecules of interest. The culture is then stopped and subjected, for example, to extraction at the optimum moment so as to obtain a maximum quantity of molecules of interest. Existing cell lines already commercially available may also be used; and Culture of tissue or organ: this type of culture may concern the root parts ("root culture"), the aerial parts ("shoot culture") or the somatic embryo. Among this type of method, cultures can undergo genomic transformation by *Agrobacterium rhizogens* (roots) or *Agrobacterium* tumefasciens (stems) bacteria. The root or aerial parts transformed this way have a high growth rate and are genetically very stable. They are used to synthesize the molecules of interest after optimization of the elicitation parameters. These cultures are then "extracted" by conventional means to recover the active plant material.

According to a still further preferred feature, the plant material according to the invention is derived from in vitro cell culture, which, as described above, advantageously makes it possible to obtain a reproducible composition rich in phenylpropanoids, in particular Forsythoside B.

More specifically, the in vitro methods of plant cell culture consist schematically:

If necessary, initially, to establish cell lines from callus (undifferentiated or dedifferentiated cell clusters) obtained on cuts of plant parts (leaf, root, stem, buds, . . . );

Selecting a cell line capable of producing on a large scale a biomass of cells according to predetermined criteria (constant phenotype and optimum and constant production of selected metabolites, ability to proliferate);

Then, from this selected line, to generate said cell biomass, possibly with an eliciting step, preferably at the end of the proliferation phase; and In a third time, in treating the cell biomass obtained in order to recover the whole cells, optionally breaking the cell aggregates by homogenization under high pressure or lysing these cells, or, if appropriate, extracting the contents of said cells, i.e. to recover a cell extract freed from cellular debris.

According to still further preferred features of the invention, the plant material derived from *Marrubium vulgare* comprises undifferentiated or dedifferentiated whole and/or lysed plant cells obtained by an in vitro cell culture method and/or a cell extract of said cells removed from cellular debris (hereinafter referred to as cellular extract).

Furthermore, according to other preferred characteristics, the plant material according to the invention comprises an effective amount of Forsythoside B as the active molecule. Proteins, amino acids, phytosterols, lipids and polysaccharides have also been identified as categories of compounds in the plant cells according to the invention.

According to the invention, undifferentiated or dedifferentiated cells of *Marrubium vulgare* may preferably be used in a spray-dried or lyophilized form. This allows their long-term storage and preserves their biological activity, but preferentially according to the invention, a cell extract is used of the undifferentiated or dedifferentiated cells of *Marrubium vulgare* free of cell debris, which advantageously makes it possible to obtain a transparent plant material having galenic qualities, such as the possibility of preparing gel type formulations more easily. The cellular content can be "recovered" and/or extracted by any physiologically acceptable solvent, or any mixture of these solvents. The extraction can be carried out according to the various known processes which can be combined: hot, by maceration, decoction, infusion, pressure, leaching, ultrasound, microwaves or by lyzing the cells by any chemical or physical process. The separation of the phases to get rid of the cellular debris can then be carried out by filtration or centrifugation. Alternatively, it is also possible to extract the biomass with a supercritical or subcritical fluid.

According to the invention, it is also possible optionally to envisage a thorough purification of the cell extract by all the methods available industrially, by liquid-liquid partitioning or chromatography, in particular using an adsorbent resin, in order to concentrate the molecules of interest such as the Forsythoside B.

Preferably, according to the invention, the physiologically acceptable medium is a hydrophilic matrix.

Preferably also, the cosmetic treatment according to the invention is topical.

To obtain the dedifferentiated or undifferentiated cells that can be used according to the invention, the following preferential method can be used:

1) From a selected line of *Marrubium vulgare*, to produce a critical pre-biomass by successive pre-cultures and increasing sizes;

2) Producing a biomass of said dedifferentiated or undifferentiated cells in a bioreactor from said pre-biomass and a suitable culture medium; and 3) Separating said biomass enriched in Forsythoside B from said culture medium and thereby recovering said dedifferentiated or undifferentiated cells.

It is possible to add an additional step to recover the cellular content of said cells freed from debris in the physiologically acceptable medium, according to one of the techniques explained above.

According to other optional features according to the invention:

4) The bioreactor production step may comprise an eliciting step, this advantageously for increasing the levels of Forsythoside B; and/or 5) The biomass from the reactor is collected by filtration after a culture time of between 7 and 21 days; Preferably between 10 and 14 days, advantageously for producing the greatest amount of biomass with great viability; and/or 6) The biomass can be subjected to a homogenization step under high pressure, in order to break up the cell aggregates; and/or 7) An additional stage of drying of the cell biomass can be added, so as to preserve it in the long term; and/or In general, elicitation of the compounds of interest can be carried out by the addition to the culture of microbial fractions (in particular *saccharomyces* yeasts): the addition to the culture of molecules of biological origin such as, for example, chitosan, methyljasmonate, jasmonic acid, salicylic acid; the addition to the culture of molecules of non-biological origin such as, for example, paclobutrazol; the application to the culture of a variation in temperature, pH or an osmotic stress induced by a non-metabolizable sugar, such as, for example, mannitol; the use of an even more drastic impoverishment of the environment in macro-elements and sugar; the addition to the culture of adsorbent resins which, in addition to eliciting the production of the compounds of interest, can trap them.

Preferably according to the invention, elicitation is carried out by modifying the culture medium, in particular the nutrient levels.

Preparation of Compositions for Implementing the Invention

A cosmetic composition according to the invention, in particular topical, comprises a plant material derived from *Marrubium vulgare*, and preferably plant cells obtained by an in-vitro cell culture process, whole or lysed, or their cell extract freed from cellular debris, in a physiologically acceptable medium. Depending on the excipient and the dosage of plant material, this composition will constitute a concentrated active ingredient or a less concentrated final composition intended for the final user.

"Physiologically acceptable medium" means according to the present invention in particular an aqueous or hydroalcoholic solution, a water-in-oil emulsion, an oil-in-water emulsion, a micro-emulsion, an aqueous gel, an anhydrous gel, a serum, a dispersion of vesicles, or a powder.

"Physiologically acceptable" means that the compositions are suitable for topical or transdermal use, in contact with mucous membranes, appendages (nails, hair and hairs), scalp and skin of mammals, particularly human, compositions which may be ingested, or injected into the skin, without risk of toxicity, incompatibility, instability, allergic response, and others.

This "physiologically acceptable medium" forms what is commonly called the excipient of the composition.

The plant material of the invention may be combined with other active ingredients at effective synergistic or reinforcing concentrations to achieve the desired effects described for the invention, such as the following: radiation filtering agents, in particular UVA and/or UVB, moisturizing, humectant, soothing, myorelaxing, slimming, restructuring, firming, plumping, tensor, smoothing, agents acting on the microcirculation, acting on inflammation, on free radicals, anti-wrinkle, lightening, acting on the radiance of the complexion, anti-glycation, pro-pigmenting, acting on the stratum corneum, on the dermal-epidermal junction, on the production of HSPs proteins, on firmness, elasticity, skin tonicity, hair regrowth, peptides, vitamins, etc.

According to the invention, the plant material can be applied on the face, the body and/or the scalp, in any appropriate form known to one skilled in the art, in particular in the form of a solution, dispersion, emulsion, paste, or powder, individually or as a premix or in vehicles individually or as a premix in vectors such as macro-, micro-, or nano-capsules, macro-, micro- or nano-spheres, liposomes, oleosomes or chylomicrons, macro-, micro- or nanoparticles, or macro-, micro- or nano-sponges, micro- or nano-emulsions, or adsorbed on organic polymer powders, talcs, bentonites, spores or exines, and other inorganic or organic supports.

In cosmetics, applications may be proposed, in particular in the skin care ranges of the face, body and/or scalp, and make-up-care ranges.

More generally, the plant material according to the present invention may be used in any form whatsoever, in a form bound to or incorporated in or absorbed in or adsorbed on macro-, micro-, and nanoparticles, or macro-, micro-, and nano-capsules, for the treatment of textiles, natural or synthetic fibers, wools, and any materials that may be used for clothing or underwear for day or night intended to come into contact with the skin, handkerchiefs or cloths, to exert their cosmetic effect via this skin/textile contact and to permit continuous topical delivery.

The CTFA («International Cosmetic Ingredient Dictionary & Handbook» (16th Ed. 2016) published by «the Personal Care Products council», ex—«the Cosmetic, Toiletry, and Fragrance Association, Inc.», Washington, D.C.), describes a non-limited wide variety of cosmetic and pharmaceutical ingredients commonly used in the skin care industry, which are suitable for use as additional ingredients in the compositions according to the present invention.

Further additional skin care actives that are particularly useful can be found in the commercial literature of Sederma and on the website www.sederma.com.

The following commercial actives can also be mentioned, as examples: betaine, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (commercial name for the acetyl hexapeptide-3 of Lipotec), spilanthol or an extract of *Acmella oleracea* known under the commercial name Gatuline Expression™, an extract of Boswellia *serrata* known under the commercial name Boswellin™ Deepaline PVB™ (Seppic), Syn-AKE™ (Pentapharm), Ameliox™, Bioxilift™ (Silab), PhytoCellTec™ Argan (Mibelle), Papilactyl D™ (Silab), Preventhelia™ (Lipotec), or the following active ingredients proposed by Sederma: Subliskin™, Venuceane™, Moist 24™, Vegesome Moist 24™, Essenskin™, Juvinity™, Revidrat™, Resistem™, Chronodyn™, Kombuchka™, Chromocare™, Calmosensine™, Glycokin factor S™, Biobustyl™, Idealift™, Ceramide 2™ Ceramide A2™, Ceramide HO3™, Legance™, Intenslim™, Prodizia™, Beautifeye™, NG-shea butter unsaponifiables (natural grade), Zingerslim™, Meiritage™, Senestem™, Sebuless™ Majestem™, Apiscalp™, Rubistem™ or mixture thereof.

Among plant extracts (in the form of classical extracts or prepared in vitro) which can be combined with the plant material from *Marrubium vulgare* of the invention, there may more particularly be mentioned extracts of Ivy, in particular English Ivy (*Hedera Helix*), of *Bupleurum chinensis*, of *Bupleurum falcatum*, of arnica (*Arnica montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hypericum perforatum*), of butcher's-broom (*Ruscus aculeatus* L), of European meadowsweet (*Filipendula ulmaria* L), of big-flowered Jarva tea (*Orthosiphon staminicus benth*), of artichoke (*Cynara scolymus*), of algae (*Fucus vesiculosus*), of birch (*Betula alba*), of green tea, of cola nuts (*Cola nipida*), of horse-chestnut, of bamboo, of *Centella asiatica*, of heather, of *fucus*, of willow, of mouse-ear, of escine, of cangzhu, of *chrysanthellum indicum*, of the plants of the *Armeniacea* genus, *Atractylodis platicodon*, *Sinnomenum, Pharbitidis, Flemingia*, of *Coleus* such as *C. forskohlii, C. blumei, C. esquirolii, C. scutellaroides, C. xanthantus* and *C. barbatus*, such as the extract of root of *Coleus barbatus*, extracts of *Ballote*, of *Guioa*, of *Davallia*, of *Terminalia*, of *Barringtonia*, of *Trema*, of *Antirobia, Cecropia, Argania, Dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), Manjistha (extracted from plants of the genus *Rubia*, particularly *Rubia cordifolia*), and Guggal (extracted from plants of the genus *Commiphora*, particularly *Commiphora mukul*), kola extract, chamomile, red clover extract, *Piper methysticum* extract (Kava Kava™ from Sederma), *Bacopa monieri* extract (Bacocalmine™ from Sederma) and sea whip extract, extracts of *Glycyrrhiza glabra*, of mulberry, of *Melaleuca* (tea tree), of *Larrea divaricata*, of *Rabdosia rubescens*, of *Euglena gracilis*, of *Fibraurea recisa hirudinea*, of *Chaparral sorghum*, of sun flower extract, of *Enantia chlorantha*, of *Mitracarpe* of *Spermacocea* genus, of *Buchu barosma*, of *Lawsonia inermis* L., of *Adiantium capillus-veneris* L., of *Chelidonium majus*, of *Luffa cylindrica*, of Japanese Mandarin (*Citrus reticulata blanco* var. *unshiu*), of *Camelia sinensis*, of *Imperata cylindrica*, of *Glaucium Flavum*, of *Cupressus Sempervirens*, of *Polygonatum multiflorum*, of *loveyly hemsleya*, of *Sambucus nigra*, of *Phaseolus lunatus*, of *Centaurium*, of *Macrocystis pyrifera*, of *Turnera diffusa*, of *Anemarrhena asphodeloides*, of *Portulaca pilosa*, of *Humulus lupulus*, of *Coffea Arabica*, of

*Ilex paraguariensis*, or of *Globularia cordifolia*, of *Albizzia julibrissin*, of *Oxydendron arboretum*, of *Zingimber Zerumbet Smith*, of *Astragalus membranaceus*, of *Atractylodes macrocephalae*, of *Plantago lanceolata*, of *Leontopodium alpinum*, of *Mirabilis jalapa* or of *Apium graveolens* or of orchids.

The compositions of the present invention may include one or more peptides, including, without limitation, the di-, tri-, tetra-, penta- and hexapeptides and their derivatives. According to a particular embodiment, the concentration of the additional peptide, in the composition, ranges from $1\times10^7$% and 20%, preferably from $1\times10^6$% and 10%, preferably between $1\times10^5$% and 5% by weight.

According to the present invention, the term "peptide" refers to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (beta-AH), YR, VW, NF, DF, KT, KC, CK, KP, KK, TT, PA, PM or PP.

Suitable tripeptides for use herein include, but are not limited to RKR, HGG, GHK, GGH, GHG, KFK, KAvaK, KI3AK, KAbuK, KAcaK, KPK, KMOK, KMO2K, PPL, PPR, SPR, QPA, LPA or SPA.

Suitable tetrapeptides for use herein include but are not limited to RSRK (SEQ ID NO: 1), GQPR (SEQ ID NO: 2) or KTFK (SEQ ID NO: 3), KTAK (SEQ ID NO: 4), KAYK (SEQ ID NO: 5) or KFYK (SEQ ID NO: 6).

Suitable pentapeptides include, but are not limited to KTTKS (SEQ ID NO: 7). Suitable hexapeptides include but are not limited to GKTTKS (SEQ ID NO: 8) and VGVAPG (SEQ ID NO: 9).

Other suitable peptides for use herein include, but are not limited to: lipophilic derivatives of peptides, preferably palmitoyl derivatives, and metal complexes as aforementioned (e.g. copper complex of the tripeptide HGG). Preferred dipeptide include for example N-Palmitoyl-beta-Ala-His, N-Acetyl-Tyr-Arg-hexadecylester (Calmosensine™, Idealift™ from Sederma). Preferred tripeptide derivatives include for example N-Palmitoyl-Gly-Lys-His and Pal-Gly-His-Lys (Pal-GKH and Pal-GHK from Sederma), the copper derivative of HGG (Lamin™ from Sigma), Lipospondin (N-Elaidoyl-KFK) and its analogs of conservative substitution, N-Acetyl-RKR—NH$_2$ (Peptide CK+), N-Biot-GHK (from Sederma), Pal-KAvaK, Pal-KI3AlaK, Pal-KAbuK, Pal-KAcaK, Pal-KMO$_2$K (Matrixyl Synthe'6™ from Sederma) and derivatives thereof.

The anti-aging tripeptides of general formula X-Pro*-Pro*-Xaa-Y described in the patent application WO2015181688 can also be cited here, with Xaa selected from Leu, Arg, Lys, Ala, Ser, and Asp, at the N-terminus end, X selected from H, —CO—R$_1$ and —SO$_2$—R$_1$ and at the C-terminal end Y is chosen from OH, OR$_1$, NH$_2$, NH$_{R1}$ or NR$_1$R$_2$, R$_1$ and R$_2$ being chosen, independently of one another, in the group comprising an aryl, aryl, aralkyl, alkylaryl, alkoxy and aryloxy group which can be linear, branched, cyclic, polycyclic, unsaturated, hydroxylated, carbonylated, phosphorylated and/or sulfurated, said group possessing in its backbone a heteroatom, in particular O, S and/or N, and Pro* corresponding to Proline, an analog or a derivative thereof; including, for example, Myr-PPL-OH and Myr-PPR—OH.

Also suitable herein are the pro-pigmenting and/or pro-mec dipeptides and tripeptides of general formula X-(Xaa1)n-Pro*-Xaa2-Y described in the patent application WO 2014/080376, with n=0, 1 or 2, Xaa1 being a hydrophobic amino acid selected from Ala, Val, Met, Leu, Iso, Phe, Pro, and analogs or derivatives thereof; or a polar amino acid selected from Ser, Thr, Tyr, Asp, Glu and derivatives and analogues thereof; and when n=2, the two amino acids Xaa1 may be identical or different; Xaa2 being a hydrophobic amino acid selected from Ala, Val, Met, Leu, Iso, Phe, and analogs or derivatives thereof; a basic amino acid selected from Arg, Lys, His, and derivatives and analogues thereof; at the N-terminus end of the peptide, X being selected from H, —CO—R$_1$ and —SO$_2$—R$_1$; at the C-terminus end of the peptide, Y being selected from OH, OR$_1$, NH$_2$, NHR$_1$ or NR$_1$R$_2$, R$_1$ and R$_2$ being, independently of one another, chosen from an alkyl, aryl, aralkyl, alkylaryl, alkoxy and aryloxy group, which may be linear, branched, cyclic, polycyclic, unsaturated, hydroxylated, carbonylated, phosphorylated and/or sulfurated, said group possessing in its backbone a heteroatom, especially O, S and or N; Pro* corresponding to Proline, an analog or a derivative thereof; which includes, for example, the peptides Pal-SPR—OH, Pal-PA-OH, Pal-PA-OH, Pal-QPA-OH, Pal-LPA-OH, Myr-SPA-OH and Pal-PP—OH.

Suitable tetrapeptide derivatives for use according to the present invention include, but are not limited to, N-Pal-GQPR (SEQ ID NO: 10) (from Sederma), Pal-KTFK (SEQ ID NO: 11) or Ela KTFK (SEQ ID NO: 12), Ela-KTAK (SEQ ID NO: 13), Ela-KAYK (SEQ ID NO: 14) or Ela-KFYK (SEQ ID NO: 15). Suitable pentapeptide derivatives for use herein include, but are not limited to, Pal-KTTKS (SEQ ID NO: 16) (available as Matrixyl™ from Sederma), N-Pal-Tyr-Gly-Gly-Phe-X (SEQ ID NO: 17) with X being Leu or Pro, N-Pal-His-Leu-Asp-Ile-Ile-X with X being Trp, Phe, Tyr, Tic, 7-hydroxy-Tic or Tpi (SEQ ID NO:18), or mixture thereof. Hexapeptide derivatives comprise the N-Pal-VGVAPG (SEQ ID NO: 19), Pal-GKTTKS (SEQ ID NO: 20) and their derivatives. The mixture of Pal-GHK and Pal-GQPR (SEQ ID NO: 10) (Matrixyl™ 3000, Sederma) can also be mentioned.

The preferred compositions commercially available containing a tripeptide or a derivative include Biopeptide-CL™, Maxilip™, Biobustyl™, Procapil™ and Matrixyl™ synthe'6™ of Sederma. The compositions commercially available preferred sources of tetrapeptides include Rigin™, Eyeliss™ Matrixyl™ Reloaded and Matrixyl 3000™ which contain between 50 and 500 ppm of Pal-GQPR (SEQ ID NO: 10) and an excipient, proposed by Sederma.

The following marketed peptides can be mentioned as well as additional active ingredients:

Vialox™ (INCI name=Pentapeptide-3 (synthetic peptide comprising alanine, arginine, isoleucine, glycine and proline)), Syn-ake™ (13-Ala-Pro-Dab-NH-Bz1) or Syn-Coll™ (Pal-Lys-Val-Lys-OH) marketed by Pentapharm;

Argireline™ (Ac-Glu-Glu-Met-Gln-Arg-Arg-NH$_2$ (INCI name=Acetyl hexapeptide-3) (SEQ ID NO: 21), Leuphasyl™ (Tyr-D-Ala-Gly-Phe-Leu) (SEQ ID NO: 22), Aldenine™ (Gly-His-Lys), Trylagen™ (INCI name=*Pseudoalteromonas* Ferment Extract, Hydro lyzed Wheat Protein, Hydro lyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-β-Ala-His-Ser-His)(SEQ ID NO: 23), Serilesine™ (Ser-Ile-Lys-Val-Ala-Val) (SEQ ID NO: 24) or Decorinyl™ (INCI name: Tripeptide-10 Citrulline=reaction product of Citrulline and Tripeptide-10 (synthetic peptide constituted of aspartic acid, isoleucine and lysine) marketed by Lipotec;

Collaxyl™ (Gly-Pro-Gln-Gly-Pro-Gln (SEQ ID NO: 25)) or Quintescine™ (Cys-Gly) marketed by Vincience;

Cytokinol™ LS (casein hydrolysate) marketed by Les Laboratoires Serobiologiques/Cognis;

Kollaren™ (Gly-His-Lys), IP2000™ (Pal-Val-Tyr-Val) or Meliprene™ (INCI name=Monofluoroheptapeptide-1: reaction product of acetic acide and a synthetic peptide comprising arginine, glycine, glutamic acid, histidine, norleucine, p-fluorophenylalanine and tryptophan) marketed by l'Institut Europeen de Biologie Cellulaire;

Neutrazen™ (Pal-His-D-Phe-Arg-$NH_2$) marketed by Innovations; or

BONT-L-Peptide™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name=Palmitoyl Tripeptide-28: reaction product of palmitic acid and Tripeptide-28 (synthetic peptide constituted of arginine, lysine and phenylalanine) marketed by Infinitec Activos.

More specifically, according to the invention, the plant material derived from *Marrubium vulgare* may be combined with at least one of the compounds selected from the compounds of vitamin B3, compounds such as niacinamide or tocopherol, retinoid compounds such as retinol, hexamidine, α-lipoic acid, resveratrol or DHEA, hyaluronic acid, peptides, especially N-acetyl-Tyr-Arg-O-hexadecyl, Pal-VGVAPG (SEQ ID NO: 19), Pal-KTTKS (SEQ ID NO: 16), Pal-GHK, Pal-KMO2K and Pal-GQPR (SEQ ID NO: 10), which are conventional active ingredients used in topical cosmetic or dermo-pharmaceutical compositions.

The present invention also provides a cosmetic or dermatological topical treatment method for improving the appearance and general condition of the skin and its appendages, in particular for tightening the pores, including the topical application to the skin of a subject in need thereof of an effective amount of plant material derived from *Marrubium vulgare* or a composition comprising it in a physiologically acceptable excipient. The treatment according to the invention makes it possible to treat skins having imperfections, in particular an inhomogeneous skin grain due to the presence of enlarged pores, and skins (including the scalp) with an oily tendency.

"Topical treatment" or "topical use" means according to the invention an application which is intended to act at the place where it is applied: skin, mucosa, appendages.

The composition comprising the plant material derived from *Marrubium vulgare* according to the invention can be applied locally to the targeted zones.

For the use according to the invention, the effective amount of the active ingredient in the composition, that is to say its dosage, depends on various factors, such as the age, the condition of the skin of the patient, etc. An effective amount means a non-toxic amount enough to achieve the desired effect.

The effective levels of Forsythoside B in the cosmetic compositions/formulations for the treatment according to the invention and intended for the user are generally between 1 ppm and 50 ppm, preferably between 3 ppm and 25 ppm, more preferably between 5 and 10 ppm relative to the total composition weight.

All percentages and ratios used herein are by weight of the total composition and all measurements are made at 25° C. unless it is otherwise specified.

For example, for a face cosmetic treatment, the European Cosmetics Directive has set a standard amount for applying a cream of 1.54 mg/day/person, which gives a standard indication of the dosages per day and person for a cosmetic treatment according to the invention of the pores of the face.

According to other specific features, the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing a composition comprising the plant material of the invention, and in a second compartment a composition containing another active ingredient and/or excipient, the compositions contained in the said first and second compartments in this case being considered to be a combination composition for simultaneous, separate or stepwise use in time.

The treatment method according to the invention is more particularly adapted to a cosmetic treatment to tighten the pores of the skin, to improve the grain, i.e. the micro-relief, and the oily and shiny appearance of the skin. The treatment according to the invention is therefore more particularly adapted to skins with an oily tendency, advantageously giving them a matting effect. The treatment according to the invention is also effective in treating the pores of the scalp.

DETAILED DESCRIPTION

The present invention will be better understood and other advantages will appear in the light of the detailed description which follows of an example of preparation of a preferred plant material according to the invention obtained in vitro and of results of in vivo tests obtained with this plant material.

The accompanying FIGS. 1 to 4 illustrate the various tests.

FIG. 1 presents a series of three successive images to illustrate the different steps making it possible, with the aid of an image processing software, to quantify the comedones of the wings of the nose.

A) EXAMPLE OF IN VITRO PREPARATION OF A PLANT CELLULAR EXTRACT

Creating a Cell Line

Figure 1:
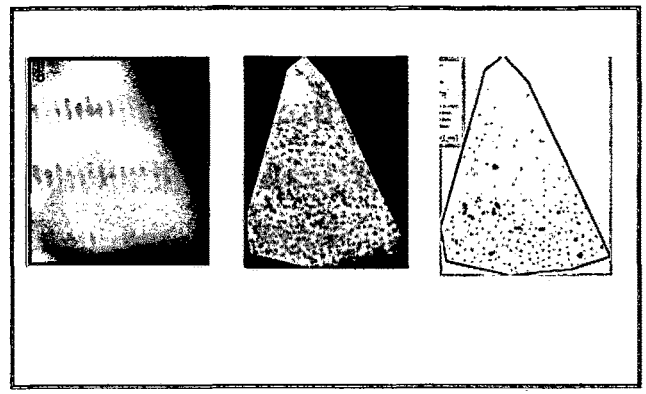

Selected pieces of leaves of the genus *Marrubium vulgare* are collected, washed and cut into small pieces of a few mm, so as to produce from 200 to 1500 explants. After a series of decontamination and sterilization treatments, the pieces are placed on an agar culture medium in the presence of a nutrient medium containing plant growth hormones in order to induce callogenesis (formation of a callus).

After a suitable period of time a cluster of dedifferentiated cells or a callus is formed, which is transferred over a larger surface and into a fresh culture medium in order to multiply. A number of subcultures (transfers to a fresh culture medium) are carried out in order to stabilize the cell line, that is to say until a high and constant rate of proliferation, a phenotype conservation, a constant content of bioactive compounds of interest (primary and secondary metabolites) are obtained.

The cell line is then subjected to a selection step which consists in culturing the cells for an appropriate period of time, taking the aggregates of cells formed and inoculating them in a liquid culture medium for a period of time which makes it possible to obtain the multiplication of the cellular aggregate. The best cell line will be that offering as quickly as possible and reproducibly a large biomass with an optimal content of selected metabolites, the best biological activity and a homogeneous phenotype.

This cell line was also chosen for its ability to produce Forsythoside B in a minimum amount of about 350 ppm by weight based on the dry weight of the cells as measured by HPLC.

Industrial Process for Obtaining a Biomass of Undifferentiated or Dedifferentiated Cells of *Marrubium vulgare* and Treatment of this Biomass Starting from a cell line prepared as described above or from an existing line.

The *Marrubium vulgare* line is initially multiplied to obtain a sufficient amount of dedifferentiated cell biomass in order to carry out the large-scale production step.

The following steps are implemented:

a) Inoculation of the selected line in a liquid medium and culture for a sufficient time to obtain a biomass increase of at least 300%;

b) Optionally transferring the suspension obtained in a) into a fresh liquid medium and re-culturing for a sufficient time to obtain a biomass increase of at least 300%;

c) Optionally, repeating step b);

d) Transferring the cell suspensions obtained in steps a) to c) into a bioreactor with fresh liquid medium, and conducting the culture under such conditions and for a time sufficient to obtain a cellular biomass containing the metabolites of interest i.e. phenylpropanoids glycosides comprising the Forsythoside B in sufficient quantities, this stage of production in bioreactor comprising an elicitation step carried out by modifying the nutrient levels of the culture medium The Bioreactor:

Volume: 5 to 50 times greater than the volume of biomass used as inoculum; the internal surface of the bioreactor is smooth and uniform (no edges or angles that could break the cell walls).

Culture Conditions:

Culture medium: a medium comprising mineral salts (a solution of macro-elements and micro-elements), vitamins, plant hormones and sucrose. Vegetable agar is added to the solid media.

Temperature: between 15° C. and 35° C., preferably between 20° C. and 30° C. and even more preferably at 25° C.

Duration: between 7 and 21 days, preferably between 10 and 14 days.

Biomass agitation: it is important that the biomass be aerated optimally, and at the same time be kept agitated either by internal means or by external means. It is necessary that the agitation, although weak, be effective, especially in the final stages, when the biomass is in large quantity. For the purposes of the present invention, suitable internal stirring means are propellers rotating at between 20 and 120 rpm, preferably at 60 rpm, or externally preferably rotating orbiting stirring means at between 40 and 200 rpm and preferably at about 120 rpm.

Oxygenation: normally carried out using sterile air at a flow rate of 0.5 to 4 liters per minute, preferably between 2 and 2.5 liters per minute, for a volume of 10 liters of biomass. Alternatively, gas mixtures containing from 10% to 100% v/v of oxygen may be used. It is preferable to use means for diffusing air or oxygen with a nozzle having a flow rate of between 10 ml/min and 600 ml/min and preferably between 50 ml/min and 350 ml/min.

Treatment of the Biomass Obtained:

Filtration to remove the culture medium and recover the cell biomass. This biomass can be characterized by its equivalent content of lyophilized cells.

Characterization of the active compounds contained in cells by analytical determination of primary and secondary metabolites produced by the culture comprising protein content, phenylpropanoids glycosides including Forsythoside B.

Extraction of the cellular content of the cells by grinding, lysis or breaking of the cells and separation of the liquid and solid phases (by centrifugation or filtration or equivalent), in order to obtain a cell extract freed of its cellular debris.

Optionally, the cellular extract is purified on a resin to increase the Forsythoside B content.

B) PREPARATION OF AN ACTIVE INGREDIENT FOR THE USE ACCORDING TO THE INVENTION

The plant material is mixed with a physiologically acceptable medium forming the excipient.

In the case of plant material obtained by in vitro cell culture as described above in point A), by way of a preferred example, this physiologically acceptable medium is, according to the invention, a hydrophilic matrix in which the plant cells are suspended or comprising the cellular content of said cells. In the case of a cosmetic composition, the hydrophilic matrix is, for example, composed of glycerol and/or butylene glycol.

An active ingredient for a cosmetic use may thus be formed for implementing the invention, comprising for example 20% by weight of cellular extract of fresh biomass of whole dedifferentiated cells (corresponding to approximately 1-2% of dry cells), in a physiologically acceptable excipient mixture consisting of glycerol (about 80%), said ingredient having a final minimum level of about 0.035% of Forsythoside B. This ingredient is then usable to prepare cosmetic formulations as disclosed below at Galenic F) representing between 0.3 and 15%, preferably between 1 and 5%, more preferably between 2 and 3% and generally 2% by weight of said formulation.

Obviously according to the invention it is possible to use a plant material comprising a different level of Forsythoside B, in particular higher, or obtained directly by the in vitro method (for example by means of an appropriate elicitation enabling the rate to be increased), or obtained by a phase of purification/concentration of the cells obtained (for example by a concentration step after extraction of the cellular content).

For example, it is possible to manufacture plant cells in the form of a purified cellular extract comprising a high level of Forsythoside B, for example a level greater than 10% relative to the dry matter, said cells being themselves used to make an active ingredient as explained above.

C) GALENIC

Various cosmetic formulations are described below using a plant material according to the invention consisting of a cellular extract of *Marrubium vulgare* obtained in vitro. Additional active ingredients, optionally in support and/or in addition to the activity of the active ingredient according to the invention, may be added in the appropriate phase according to their hydrophobic or hydrophilic nature. These ingredients can be of any category according to their function(s), the place of application (body, face, neck, bust, hands, etc.), the final effect sought and the targeted consumer, in particular anti-wrinkle, moisturizer, for treating dark circles, firming, anti-glycation, volumizing, soothing, myo-relaxing, anti-redness, detoxifying, etc.

Active Ingredient According to the Invention Used in the Galenic Formulations Given Below:
  ingredient described in point B) above.
  1) Cream Form (in Particular Used for the In Vivo Tests Presented Below at Point D)

| Ingredient (INCI name) | Function | Weight % |
|---|---|---|
| Part A | | |
| H₂O (Aqua) | — | qsp100 |
| Carbopol Ultrez 10 (Carbomer) | Rheology modifier | 0.30 |
| Part B | | |
| Brij S2-SS-(RB) (Steareth-2) | Emulsifier H/E | 0.40 |
| Brij S10-SO-(RB) (Steareth-10) | Emulsifier H/E | 1.20 |
| Crodafos CES-PA-(RB) (Cetearyl Alcohol (and) Dicetyl Phosphate (and) Ceteth-10 Phosphate) | Emulsifier H/E | 4.00 |
| Laurocapram | Emollient | 2.50 |
| Cyclopentasiloxane (and) Cyclohexasiloxane | Emollient | 2.00 |
| Crodamol OSU-LQ-(JP) (Diethylhexyl Succinate) | Emollient | 4.00 |
| Crodamol AB-LQ-(RB) (C12-15 Alkyl Benzoate) | Emollient | 3.00 |
| Part C | | |
| Glycerin (Glycerin) | Humectant | 4.00 |
| Octanediol (Caprylyl Glycol) | Biocide | 0.50 |
| Part D | | |
| Phenoxyethanol | Preservative | qs |
| Part E | | |
| Potassium sorbate | Preservative | qs |
| Part F | | |
| H₂O (Aqua) | — | 4.00 |
| NaOH 30% (Sodium Hydroxide) | pH adjuster | 0.40 |
| Part G | | |
| Ingredient according to the invention | Active | 2.00 |
| Part H | | |
| Fragrance | Perfume | 0.10 |

Protocol: Swell part A without stirring for 30 minutes and then heat at 75° C. using a water bath. Heat part B at 75° C. using a water bath. Melt part C at 45° C. Mix part D in part C, previously cooled. Pour part C + D into part A under stirring. Add part B in the previous phase, under rapid stirring. Add part E extemporaneously in the previous phase under stirring. Add after successive homogenization parts F, G, and H.

Examples of Ingredients Marketed by Sederma that can be Added to this Formulation:
  REVIDRATE™: active that in particular improves the cohesion of the epidermis and its hydration.
  MATRIXYL synthe'6™: anti-wrinkle ingredient comprising the Palmitoyl Tripeptide-38 which helps repair skin damage caused by aging.
  MAJESTEM™: active agent based on plant cells obtained by in vitro cell culture titrated in leontopodic acid; tightens the sagging neck skin, lifts the cheeks smoothes out wrinkles around the eyes, especially crow's feet wrinkles.
  PRODIZIA™: active ingredient comprising an extract of *Albizia julibrissin*, fighting the signs cutaneous fatigue: dark circles, under eye bags, dull complexion and drawn features, by repairing and protection the skin against the caused by damages of glycation and glycoxydation.
  CALMOSENSINE™: soothing active for sensitive skins comprising the Tyr-Arg lipo-dipeptide. It reduces discomfort feelings.
  SUBLISKIN™: active ingredient that moisturizes and smooths the skin while allowing it to resist to external aggressions.

2) Serum Form

| Ingredient (INCI name) | Function | Weight % |
|---|---|---|
| Part A | | |
| Demineralized water (Aqua) | — | qsp 100 |
| Potassium sorbate | Preservative | qs |
| Partie B | | |
| Zemea ® (Propanediol) | Humectant | 3.00 |
| Keltrol ™ CG-SFT (Xanthan Gum) | Rheology modifier | 0.50 |
| Supercol ™ GF (*Cyamopsis Tetragonoloba*) (Guar) Gum) | Rheology modifier | 0.15 |
| Phenoxyethanol | Preservative | Qs |
| Crodesta ™ F-50 (Sucrose Distearate) | Emulsifier H/E | 1.50 |
| Crodesta ™ F-160 (Sucrose Stearate) | Emulsifier H/E | 0.50 |
| Part C | | |
| Crodamol ™ SS (Cetyl Esters) | Emollient | 0.50 |
| Pripure ™ 3759 (Squalane) | Emollient | 5.00 |
| Crodamol ™ IPIS (Isopropyl Isostearate) | Emollient | 3.00 |
| Part D | | |
| Demineralized water (Aqua) | — | 0.60 |
| Lactic acid | pH adjuster | 0.03 |
| Part E | | |
| Ingredient according to the invention | Active | 2.00 |
| Part F | | |
| Fragrance | Perfume | 0.10 |

Protocol: Add part A to part B under stirring and heat at 75° C. using a water bath. Heat part C at 75° C. using a water bath. Add part C to part A + B under stirring. Adjust pH to 5.50 +/− 10 with part D. Add part E below 45° C. Add part F below 35° C.

Examples of Ingredients Marketed by Sederma that can be Added to this Formulation:
  EVERMAT™: active that associates an extract of *Enantia chlorantha* rich in protoberberins and oleanolic acid, which reduces pore size and shine, and refines skin grain.
  RESISTEM™: anti-aging active, helping the skin to build its own anti-aging defense system, based on an extract obtained by cell culture of *Globularia cordifolia* plant.
  HALOXYL™: active ingredient for eye contour treatment that resorbs the dark circles.

3) Galenic Form for a Tissue Mask (Clear Transparent Liquid)

| Ingredient (INCI name) | Function | Weight % |
|---|---|---|
| Part A | | |
| Demineralized water (Aqua) | — | qsp 100 |
| Sodium sulfite | Anti-oxidant | 0.01 |
| Potassium sorbate | Preservative | Qs |
| Part B | | |
| Butylene Glycol | Humectant | 8.00 |
| Keltrol ™ CG-SFT (Xanthan Gum) | Rheology modifier | 0.30 |
| Phenoxyethanol | Preservative | qs |
| Part C | | |
| Demineralized water (Aqua) | — | 0.10 |
| Lactic acid | pH adjuster | 0.01 |
| Part D | | |
| Ingredient according to the invention | Active | 4.00 |
| Part E | | |
| Fragrance 3 | Perfume | 0.05 |

Protocol: Prepare parts A and B. Add part B to part A under stirring. Prepare part C. Add part C. Then homogenize part D. Homogenize well. Add the tissue mask to the product. Leave 2 min before use.

Examples of Ingredients Marketed by Sederma that can be Added to this Formulation:

EYELISS™: active ingredient that helps prevent against the appearance of bags under the eyes. It combines three components: hesperidin methyl chalcone reducing capillary permeability, Valyl-Tryptophan (VW) dipeptide which promotes lymphatic circulation and Pal-GQPR lipopeptide that improves firmness, elasticity and reduces inflammation.

MATRIXYL 3000™: peptide-based anti-wrinkle ingredient comprising two matrikines Pal-GHK and Pal-GQPR, which in synergy helps repairing skin damages caused by aging.

WONDERLIGHT™: active comprising a powder of *Humulus lupulus* (Hops) strobile in a liposoluble excipient, which helps reduce hyperpigmentation accentuated by age and stress: lentigines, ephelides, post-inflammatory spots and melasma.

4) Cleansing Lotion Form

| Ingredient (INCI name) | Function | Weight % |
|---|---|---|
| Part A | | |
| Demineralized water (Aqua) | — | qsp 100 |
| Sodium sulfite | Anti-oxidant | 0.01 |
| Partie B | | |
| Zemea ® (Propanediol) | Humectant | 4.00 |
| Activsoft ™ S (*Cyamopsis Tetragonoloba* (Guar) Gum) | Rheology modifier | 0.20 |
| Phenoxyethanol | Preservative | Qs |
| Versaflex ™ V-175 (Sucrose Palmitate & Glyceryl Stearate & Glyceryl Stearate Citrate & Sucrose & Mannan & Xanthan Gum) | Emulsifier H/E | 1.00 |
| Partie C | | |
| Crodamol ™ AB (C12-15 Alkyl Benzoate) | Emollient | 5.00 |
| Crodamol ™ GTCC (Caprylic/Capric Triglyceride) | Emollient | 5.00 |
| Partie D | | |
| Potassium Sorbate | Preservative | Qs |
| Part E | | |
| Demineralized water (Aqua) | — | 0.50 |
| Lactic acid | pH adjuster | 0.05 |
| Part F | | |
| Crodasinic ™ LS30 (Sodium Lauroyl Sarcosinate & Aqua) | Savon | 1.00 |
| Part G | | |
| Ingredient according to the invention | Active | 3.00 |
| Part H | | |
| Fragrance | Perfume | 0.10 |

Protocol: Prepare parts A and B. Pour part B into part A under stirring. Prepare part C and add it. Thoroughly homogenize. Add successively parts D, E, F, G and H while homogenizing well.

Examples of Ingredients Marketed by Sederma that can be Added to this Formulation:

OPTIM HYAL™: active ingredient obtained by bio-fermentation, contains Glycokines™, oligosaccharides of acetylated glucuronic acids having a structure similar to hyaluronic acid fragments; smoothes wrinkles, rehydrates on the surface and in depth; enhances the flexibility and resistance of the skin.

SEBULESS™: purifying sebo-regulator ingredient comprising a *Syringa vulgaris* extract, which mattifies and refreshes complexion, fades the inflammatory blemishes.

5) Atomizer Form

| Ingredient (INCI name) | Function | Weight % |
|---|---|---|
| Part A | | |
| Demineralized water (Aqua) | — | qsp 100 |
| Potassium sorbate | Preservative | qs |
| Escalol ™ 577 (Benzophenone-4)[3] | UV filter | 2.00 |
| Alcool | Solvent | 5.00 |
| Part B | | |
| Pentylène Glycol | Humectant | 5.00 |
| Crovol ™ A70 (PEG-60 Almond Glycerides) | Emollient | 1.00 |
| Phenoxyethanol | Preservative | Qs |
| Tween ™ 20 (Polysorbate 20) | Solubilizer | 0.20 |
| Fragrance | Perfume | 0.20 |
| Part C | | |
| Demineralized water (Aqua) | — | 10.00 |
| Sodium hydroxyde 30% | pH adjuster | 1.00 |
| Part D | | |
| Ingredient according to the invention | Actif | 2.00 |

Protocol: Prepare part A and part B. Pour part B into part A under stirring. Prepare part C and add it. Thoroughly homogenize. Add part D. Mix well.

Examples of Ingredients Marketed by Sederma that can be Added to this Formulation:

AQUALANCE™: osmo-protector moisturising active ingredient comprising homarine and erythritol.

PACIFEEL™: active ingredient comprising a natural extract of the *Mirabilis jalapa* plant also known as the Marvel of Peru, which alleviates cutaneous discomfort, fades redness of sensitive and reactive skin and strengthens and hydrates the epidermis.

D) IN VIVO STUDIES

Principle

The evaluation of the efficacy of the ingredient according to the invention was carried out on 65 volunteers in two independent studies:

A study focused specifically on the analysis of pores and comedones by image analysis on different types of standardized photographs.

A study of the mico-relief (MDN: "Microdepressionary network") of the skin (homogenization and smoothing), by VISIA™ image analysis and fringe projection.

1) Analysis of Pores and Comedones

A pore of the face is defined by an enlarged (dilated) opening of the sebaceous follicles, which appear as empty structures in the shape of a funnel or as cylindrical plugs corresponding to comedones, also called "blackheads" when the latter show coloration. The tests were carried out on these plugs which were quantified by photographing them, either directly on the face or after extraction with the aid of patches.

Protocol

Specific Inclusion Citeria

The study was carried out on a panel of 40 male or female volunteers of mean age 44 years (21-67 years), with blackheads/comedones visible on the wings of the nose.

They were asked not to carry out aesthetic care 1 month before the 1st appointment, and throughout the study (skin cleansing, use of patch, exfoliation, mask, etc.). In addition, exposures to the sun or UV were prohibited, as well as the application of other cosmetics on the tested areas.

Type of Study, Duration and Applications

This study was conducted on the face. A cream containing 2% of the ingredient according to the invention (formula 1) in the above Galenic part C) was applied morning and evening under use conditions for 4 weeks.

The Study Synopsis can be Summarized as Follows:

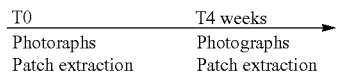

| T0 | T4 weeks |
|---|---|
| Photoraphs | Photographs |
| Patch extraction | Patch extraction |

Statistical studies were performed using Student's t-test or, if necessary, with a non-parametric Wilcoxon test. Tailed tests were performed on paired data.

Results a. Photography of the Nose Wings and Analysis of Comedones:

A HeadScan™ photo bench (from Orion concept) was used to perform a nose wing acquisition. This bench consists of a Nikon™ D7000 digital camera, a contention system and a flash system. With this system it is possible to obtain pictures of the face in a reproducible way.

The image analysis was carried out using an image analysis software. Different steps (filters, binarization, segmentation and sorting of objects according to their size/circularity) allowed to segment the original image and to quantify the comedones. FIG. 1 illustrates these various steps making it possible to extract quantifiable objects according to their size and their circularity.

TABLE 1

Variation of comedones after application of a cream containing 2% of the ingredient according to the invention (n = 40 volunteers)

|  | Mean number of comedones | | Total area occupied by the comedones (mm$^2$) | |
|---|---|---|---|---|
|  | T0 | T4 weeks | T0 | T4 weeks |
| Mean ± standard deviation | 116.6 ± 50.9 | 106.3 ± 53.4 | 6.36 ± 3.33 | 5.80 ± 3.75 |
| % change vs.T0 | Reference | −8.8% | Reference | −8.8% |
| Significance |  | p < 0.05 |  | p < 0.01 |
| Maximum |  | −50% |  | −67% |
| % Responders |  | 68% |  | 73% |

After 4 weeks of application of the cream according to the invention, there was a significant decrease in the number of comedones of −8.8% (p<0.05). At the same time, the area occupied by these comedones also decreased significantly by 8.8% (p<0.0/). From this result, a lower visibility of the pores and/or comedones on the skin and accordingly a visibly improved skin texture/grain is deduced.

b. Extraction and Standardized Photography of Comedones and Analysis of their Characteristics:

Nose wing comedones are extracted in standardized ways using an exfoliating patch (Nivea™). This patch is then photographed using a portable Nomadcam™ photographic bench (from Newtone Technologies). It consists of a Nikon™ D90 digital camera, a flash illumination system with crossed polarized light and a double colorimeter. This system ensures positioning and standardized colors.

Finally, the extraction and quantification of comedones are performed by image analysis.

TABLE 2

Variation of comedones after application of a cream containing 2% of the ingredient according to the invention (n = 40 volunteers)

|  | Number of comedones | | Mean length (in pixels) | | Mean yellowish color (parameter b*) (in pixels) | |
|---|---|---|---|---|---|---|
|  | T0 | T4 weeks | T0 | T4 weeks | T0 | T4 weeks |
| Mean | 104.2 | 56.6 | 17.3 | 14.7 | 7.4 | 6.7 |
| Standard deviation | 72.9 | 41.2 | 7.7 | 4.4 | 1.6 | 1.6 |
| % change vs.T0 |  | −45.7% |  | −15% |  | −9.5% |
| Significance |  | p < .01 |  | p < 0.01 |  | p < 0.01 |
| Maximum |  | −93% |  | −52% |  | −52% |
| Responders |  | 85% |  | 78% |  | 68% |

The result analysis shows an effect at a plurality of levels on blackheads. On the one hand, their number decreased strongly by −45% (p<0.0/), which confirms the previous results. On the other hand, their length decreases by 15% (p<0.0/), which therefore indicates a reduction in pore size. Finally, a lower coloring is also observed because the parameter b* decreases by −9.5% (p<0.0/), indicating an action of the active ingredient according to the invention on the phenomenon of oxidation of plug. All this contributes to causing a lower visibility of the comedones and therefore of the pores on the face.

c. Extraction and Standardized UV Photography of Comedones for Porphyrin Analysis:

Porphyrins are bacterial excretions located in the pores that are generally associated with oily or acne prone skin. A decrease in porphyrins may be partly due to a decrease in pore size.

The blackheads/comedones are extracted in the same way as in the previous paragraph.

Figure 2:
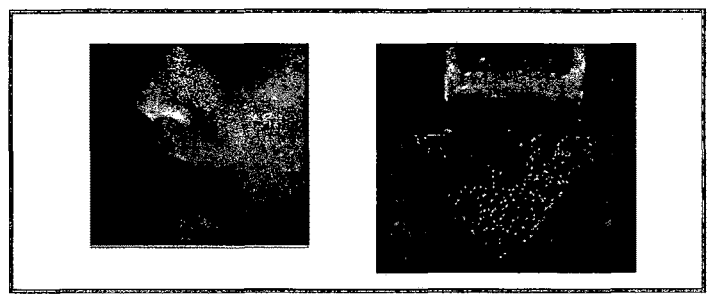
FIG. 2 shows a series of two photographs under UV light used to analyze the pores occupied by porphyrins in a given zone.

They are then photographed in a standardized way by a VISIA™ photographic bench (Canfield Company). Among other things, with the VISIA™ it is possible to obtain photos under UV light (as illustrated in the attached FIG. 2). The software integrated into the VISIA™ is then capable of extracting in a zone determined by the experimenter the number of pores occupied by porphyrins, as well as the index which takes into account the percentage of area occupied by the porphyrins but also their intensity.

TABLE 3

Variation of porphyrins after application of a cream containing 2% of the ingredient according to the invention (n = 40 volunteers)

|  | Number of points with porphyrin | | Total area occupied by the comedones (mm$^2$) | |
| --- | --- | --- | --- | --- |
|  | T0 | T4weeks | T0 | T4weeks |
| Mean ± standard deviation | 144.1 ± 65.9 | 109.4 ± 45.7 | 3.77 ± 2.10 | 2.76 ± 1.40 |
| % change vs.T0 | Reference | −24.1% | Reference | −26.8% |
| Significance |  | $p < 0.01$ |  | $p < 0.01$ |
| Maximum |  | −61% |  | −66% |
| % responders |  | 78% |  | 68% |

The result analysis shows the reduction in the amount of porphyrins and the area they occupy on the nose (−24.1% and −26.8% vs. T0, $p<0.01$ for both). This therefore indicates a reduction in the size of the pores.

Analysis of the Homogeneity and Smoothing of the Skin

A different approach was carried out during this study taking into account the micro-relief brought by the pores on the skin. The principle is that a decrease in the pores is directly correlated to a decrease in their relief. For this, a double acquisition was made on the face, by image analysis using a VISIA™ and fringe projection.

Protocol

Specific Inclusion Criteria

This study was carried out on a panel of 30 female volunteers of mean age 45 years (36-50 years), with some fine lines on the face. They were asked not to carry out aesthetic care 1 month before the 1st appointment, and throughout the study (skin cleansing, use of patch, exfoliation, mask, etc.). In addition, exposures to the sun or UV were prohibited, as well as the application of other cosmetics on the tested areas.

Type of Study, Duration and Applications

This study was carried out in a double-blind manner on the face (2% cream of the ingredient according to the invention and a placebo cream applied in contra-lateral, see formula 1) in the Galenic part C) with or without the active ingredient according to the invention). The two creams were applied in bi-daily massage for 4 weeks.

The synopsis of the study can be summarized as follows:

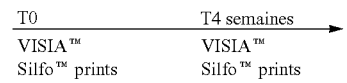

| T0 | T4 semaines |
| --- | --- |
| VISIA™ | VISIA™ |
| Silfo™ prints | Silfo™ prints |

Statistical studies were performed using Student's t-test. Tailed tests were performed on paired data.

Results a. Texture Analysis Using the VISIA™

Figure 3:
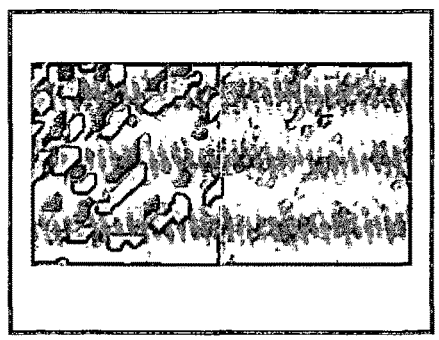
FIG. 3 shows a series of two photographs illustrating the analysis of the texture carried out using the VISIA™ apparatus.

A VISIA™ (Canfield) was used. This device allows obtaining standardized photos under different illuminations (white light, UV, polarized) and the integrated software can provide different parameters. The texture of the skin was studied (also called imperfections) which is actually a measure of the color heterogeneity between 2 areas. It thus detects the bumps and the hollows of the skin (illustrated in attached FIG. 3). The texture can be assimilated to a roughness which, on this area of the face, is linked to the pores.

TABLE 4

Variation of the texture parameter after application of a cream containing 2% of the ingredient according to the invention (n = 30 volunteers)

| Skin texture (number of imperfections) | Cream according to the invention | | Placebo | |
| --- | --- | --- | --- | --- |
|  | T0 | T4sem | T0 | T4weeks |
| Mean ± standard deviation | 982 ± 72 | 969 ± 72 | 986 ± 74 | 1045 ± 84 |
| % change vs. T0 | Reference | −1.3% | Reference | +6% |
| Significance |  | nds* |  | $p < 0.05$ |
| Maximum |  | −34% |  | −21% |
| % responders |  | 50% |  | 37% |
| % change vs.placebo |  | −7.3% | | |
| Significance |  | $p < 0.05$ | | |

*nds: non significative difference

The results show a deterioration of the skin after 4 weeks of placebo application. The number of imperfections has increased by +6% ($p<0.05$). At the same time, it can be seen that the application of the cream according to the invention makes it possible to control this deterioration in the skin texture even with a small decrease of 1.3% in the number of imperfections. This significative difference is −7.3% ($p<0.05$).

b. Analysis of Smoothing by Prints and Fringe Projection

A negative imprint of the relief of the skin of the face using a silicone polymer (Silflo®) was made on the cheek before and after application of the products. The study of the micro-relief was then carried out using a technique of fringe projection using a PRIMOS™ device (GFM) with a field of 18×13 mm. This field, specific for the micro-relief, has an excellent lateral resolution, particularly adapted to the relief of the cheek.

Figure 4:
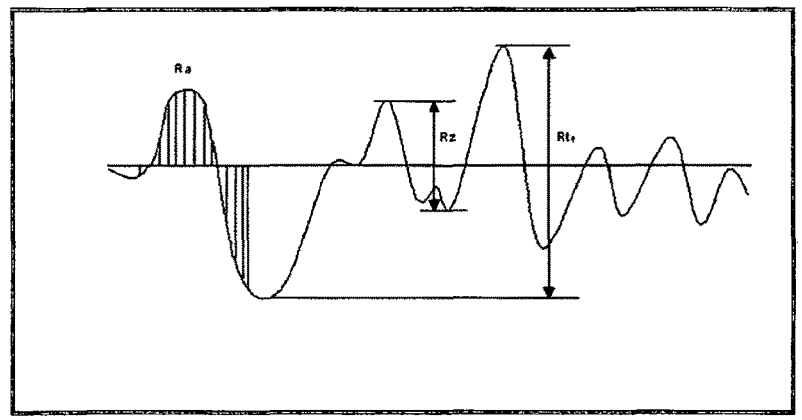
FIG. 4 shows a representation of a relief profile obtained by means of a fringe projection technique.

FIG. 4 shows a representation of a relief profile obtained with this device.

The studied parameters were:

Ra: average roughness

Rz and Rt: mean and maximum amplitude

Their reduction characterizes a smoothing effect.

TABLE 5

Variation of the microrelief after application of a cream containing 2% of the ingredient according to the invention (n = 30 volunteers)

| | Smoothing (Ra in μm) | | | | Mean depth (Rz in μm) | | | | Max depth (Rt in μm) | | | |
|---|---|---|---|---|---|---|---|---|---|---|---|---|
| | Invention cream | | Placebo | | Invention cream | | Placebo | | Invention cream | | Placebo | |
| | T0 | T4 week | T0 | T4 week | T0 | T4 week | T0 | T4 week | T0 | T4 week | T0 | T4 week |
| Mean | 9.9 | 9.0 | 9.5 | 9.5 | 44.5 | 41.7 | 43.0 | 43.5 | 64.0 | 60.0 | 62.4 | 63.1 |
| Standard deviation | ±0.5 | ±0.4 | ±0.4 | ±0.5 | ±1.9 | ±1.8 | ±1.9 | ±2.2 | ±2.7 | ±2.5 | ±2.6 | ±3.1 |
| % change vs.T0 | | −9.1% | | 0.0% | | −6.3% | | +1.2% | | −6.3% | | +1.1% |
| Significance | | $p < 0.05$ | | nds | | $p < 0.05$ | | nds | | $p < 0.05$ | | nds |
| Maximum | | −50% | | | | −43% | | | | −47% | | |
| Responders | | 67% | | | | 63% | | | | 63% | | |
| % change vs.placebo | | | −9.1% | | | | −7.5% | | | | −7.4% | |
| Significance | | | $p < 0.05$ | | | | $p < 0.05$ | | | | $p < 0.05$ | |

The application of the cream according to the invention results in a smoothing of the cheek with a decrease of −9.1% ($p<0.05$) with respect to T0. At the same time, the application of the placebo produces no effect. The effect of the cream according to the invention is superior to that of placebo (difference of −9.1%, $p<0.05$). For the mean and maximum depth parameters, a similar reduction was observed (−6.3 and −6.3%, both $p<0.05$ vs. T0).

This smoothing of the skin results in smoothing of the pores.

The invention claimed is:

1. A method for cosmetic non-therapeutical treatment for tightening skin pores comprising applying to the skin and scalp having an oily tendency of a subject in need thereof a cosmetic ingredient comprising a plant material from *Marrubium vulgare*,
   wherein said plant material comprises undifferentiated or dedifferentiated plant cells, whole and/or lysed, obtained by an in vitro cell culture process, and/or a cellular extract of said cells freed of cellular debris.

2. The method according to claim 1, wherein said plant material comprises an effective quantity of Forsythoside B as the active molecule.

3. The method according to claim 1 wherein said plant cells are suspended in a physiologically acceptable medium.

4. The method according to claim 1 of wherein said cellular extract is in a physiologically acceptable medium constituted of a hydrophilic matrix.

5. The method according to claim 1, wherein the cosmetic ingredient is topically applied to the skin.

6. The method according to claim 1, wherein the treatment improves skin grain.

7. The method according to claim 1, wherein the treatment smooths the skin.

* * * * *